United States Patent [19]

Zecher et al.

[11] 3,979,421
[45] Sept. 7, 1976

[54] REACTION PRODUCTS CONTAINING FREE ISOCYANATO GROUPS

[75] Inventors: Wilfried Zecher, Cologne-Stammheim; Rudolf Merten, Leverkusen, both of Germany

[73] Assignee: Bayer Aktiengesellschaft, Leverkusen, Germany

[22] Filed: May 10, 1968

[21] Appl. No.: 728,349

[30] Foreign Application Priority Data

May 12, 1967 Germany............................. 52393

[52] U.S. Cl.................... 260/453 P; 260/2.5 AT; 260/75 NT; 260/77.5 AT; 260/453 A; 260/453 AL; 260/453 AR; 260/454
[51] Int. Cl.............................................. C07c 119/04
[58] Field of Search...... 260/453 A, 453 P, 453 AR, 260/453 AB, 453 AL

[56] References Cited
UNITED STATES PATENTS

| | | | |
|---|---|---|---|
| 3,284,479 | 11/1966 | Windemuth et al. | 260/453 |
| 3,444,231 | 5/1969 | Merz | 260/453 |
| 3,455,981 | 7/1969 | Nash et al. | 260/453 |

OTHER PUBLICATIONS

Clemens et al., Chemical Abstracts, vol. 55, p. 23,566, (1961).

*Primary Examiner*—Lewis Gotts
*Assistant Examiner*—Dolph H. Torrence
*Attorney, Agent, or Firm*—Gene Harsh; Joseph C. Gil

[57] ABSTRACT

Reaction products containing free isocyanato groups are produced by reacting ketimines with polyisocyanates.

4 Claims, No Drawings

REACTION PRODUCTS CONTAINING FREE ISOCYANATO GROUPS

This invention relates to reaction products containing free isocyanato groups and more particularly relates to reaction products containing free isocyanato groups produced by reacting ketimines with polyisocyanates.

It has previously been known that one may react Schiff's bases of aldehydes and amines with isocyanates. Thus, a diketo triazine is obtained by reaction between N-ethyl-benzaldehyde azomethine and 2 mols of phenylisocyanate at 180° C (The Journal of the American Chemical Society, 48, 2440, [1926]). The condensation product of formaldehyde and methyl aniline reacts with 1 mol of phenyl isocyanate to form a uretdione derivative (J. Chem. Soc. 95, 504, [1909]). One mol of aldimine thus reacts by this process with 1 or 2 mols of isocyanate to form 6-membered or 4-membered ring systems, and the compounds prepared in this way no longer contain any isocyanato residues.

It is, therefore, an object of this invention to provide isocyanato-containing reaction products of Schiff's bases and a process for preparing the same. A further object of this invention is to provide high molecular weight reaction products containing free isocyanate groups from ketimines and a process for preparing the same. A still further object of this invention is to provide isocyanato-containing reaction products of ketimines which are further especially suitable for the production of lacquers, foams and the like and as bonding agents and similar utilities.

The foregoing objects and others which will become apparent from the following description are accomplished in accordance with this invention, generally speaking, by providing reaction products containing free isocyanato groups produced by reacting ketimines, that is, Schiff's bases obtained by reaction between ketones and amines, with polyisocyanates in the absence of moisture. More particularly, the objects of this invention are accomplished by reacting ketimines with polyisocyanates in the absence of moisture under reaction conditions in which from 1 to about 10 mols of polyisocyanate, such as, for example, a bi-functional or tri-functional isocyanate and the like, is used per equivalent of azomethine. If aldimines such as, for example, N-phenyl-benzaldehyde-azomethine are used under the same conditions for the reaction with isocyanates instead of the ketimines to be used according to this invention, then not more than one equivalent of isocyanate enters into the reaction per aldimine group and most of the polyisocyanate introduced into the reaction can be recovered unchanged.

Accordingly, the present invention relates to a process for the preparation of isocyanato-containing reaction products in which Schiff's bases containing at least one hydrogen atom in the α-position to the carbon atom of the C=N bond and which corresponds to the general formula

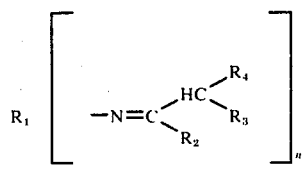

wherein $R_1$ is an n-functional organic radical, $R_2$ is an organic radical, $R_3$ and $R_4$ are hydrogen atoms or organic radicals and n is an integer of from 1 to 3, are reacted with polyisocyanates. More particularly, $R_1$ may be any suitable n-functional organic radical such as, for example, an aliphatic, cycloaliphatic, aromatic or heterocyclic radical, preferably $R_1$ is an n-functional alkyl, cycloalkyl, alkyl or cycloalkyl interrupted by hetero atoms such as O, N, or S atoms, aryl, alkaryl, aralkyl or heterocyclic radicals. $R_2$ may be any suitable organic radical similar to $R_1$ but is preferably an organic hydrocarbon radical such as, for example, an aliphatic, cycloaliphatic or aromatic radical, preferably an alkyl, cycloalkyl, aryl, aralkyl or alkaryl radical. The radicals $R_3$ and $R_4$ may be hydrogen atoms or organic radicals similar to $R_1$ but are preferably organic hydrocarbon radicals such as, for example, aliphatic, cycloaliphatic or aromatic radicals, preferably alkyl, cycloalkyl, aryl, aralkyl or alkaryl radicals. The radicals $R_2$ and $R_3$ may, however, together form a 5 to 7-membered cycloaliphatic or heterocyclic ring.

If the radicals $R_1$, $R_2$, $R_3$ and $R_4$ represent aliphatic radicals, these residues contain preferably 1 to 36 carbon atoms, if they represent cycloaliphatic radicals, these residues contain preferably 5 to 10 carbon atoms and if they represent aryl radicals, they contain preferably up to 14 carbon atoms; the aryl radicals can be connected by O, S or N atoms. If they represent alkaryl or aralkyl radicals, preferably radicals with up to 3 aryl radicals as already defined and with alkyl radicals up to 5 carbon atoms are used.

The polyisocyanates employed in the process of this invention are those which correspond to the general formulas

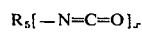

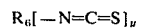

in which $R_5$ and $R_6$ are respectively x-functional and y-functional organic radicals, preferably organic hydrocarbon radicals such as alkyl, cycloalkyl, aralkyl, alkaryl or aryl radicals and x and y are integers of 2 or 3.

Alkyl radicals which are preferred contain 1 to 36 carbon atoms, cycloalkyl radicals contain preferably 5 to 10 carbon atoms, aryl radicals contain preferably up to 14 carbon atoms; the aryl radicals can be connected with O, N or S bridges, aralkyl and alkaryl radicals contain up to 3 aryl radicals as defined and alkyl radicals contain up to 5 carbon atoms.

The radical $R_1$ of the general formula (I) is preferably an n-functional alkyl derived from methane, n-, iso-, or tertiary butane, hexane, dodecane, eicosane, isopentane and the like, or propene, diethylether and dipropylsulphide, cyclopentane, cyclohexane, benzene, naphthalene, pyridine, diphenyl, diphenylmethane, diphenylsulphide, diphenylether, toluene, o-, m- or p-xylene, tris-tolyl-methane or triarylphosphate. The radical $R_1$ may also be substituted by one or more substituents, such as, for example, by alkyl, halogen, nitro, alkoxy, dialkylamino, alkylimino, arylimino, acyl, hydroxy, carbalkoxy or cyano groups.

The radicals $R_2$, $R_3$, $R_4$, $R_5$ and $R_6$ of the hereinabove set forth general formulas preferably have the meaning indicated above for $R_1$. In addition, $R_3$ and $R_4$ may also represent hydrogen atoms and $R_2$ and $R_3$ together may preferably form a cyclopentane, cyclohexane, cycloheptane or piperidine ring which may optionally be substituted one or more times by alkyl, aryl, dialkylamino, alkylamino, arylamino or carbalkoxy groups.

The Schiff's bases to be used in the process according to the invention as starting materials may be prepared by methods already known to those skilled in the art such as, for example, by condensation of ketones with primary aliphatic, araliphatic or aromatic amines and the like, optionally with the addition of a catalytic amount of catalysts.

Any suitable Schiff's bases corresponding to the general formula (I) may be used according to this invention. The following are several examples of Schiff's bases which may be used according to the invention as starting materials:

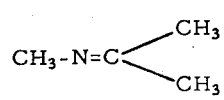 , 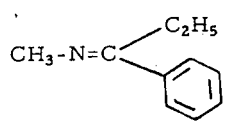 , 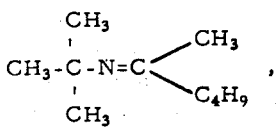 ,

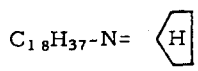 , 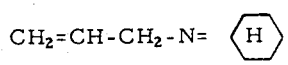 , 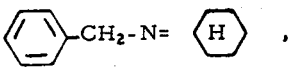 ,

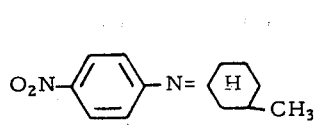 , 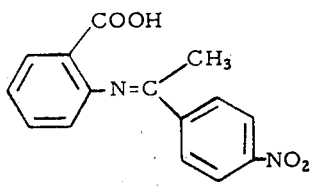 , 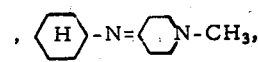 ,

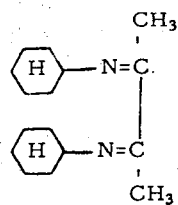 , 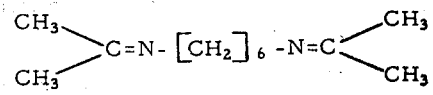 ,

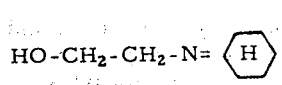 , 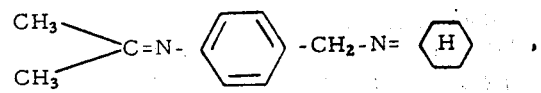 ,

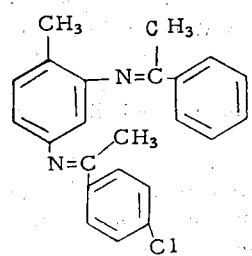 , 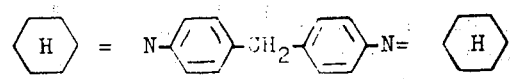

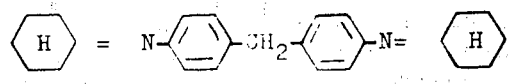

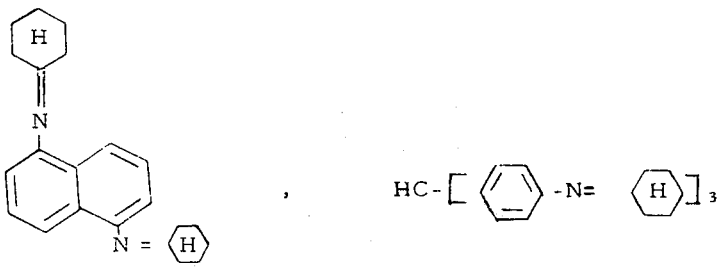

and the like.

Ketimines which contain at least two hydrogen atoms in the α-position to the carbon atom of the CN bond have been found to be especially suitable for use in the process of the invention and thus represent a preferred embodiment.

Any suitable polyisocyanates corresponding to the general formulas (II) and (III) may be used according to the process of this invention. The following are several examples of monomeric polyisocyanates which may be used in the process of the invention, the preparation of which may also be carried out by known processes: 1,6-hexamethylene diisocyanate, 1-4-butylene diisocyanate, 1,3- and 1,4-phenylene diisocyanate, 1-methyl-2,6- and 1-methyl-2,4-diisocyanato-cyclohexane and mixtures thereof, toluene-2,4- and toluene-2,6-diisocyanate and mixtures thereof, naphthylene-1,5-diisocyanate, diphenylether-4,4'-diisocyanate, diphenylmethane-4,4'-diisocyanate, 4-isocyanato-benzylisocyanate, 4,4'-diphenyl-dimethylmethane diisocyanate, 4,4',4''-thiophosphoric acid triphenylester triisocyanate, 2,4,5,6-tetrachlorophenylene-1,3-diisocyanate, xylylene diisocyanate and the like. Instead of the polyisocyanates, one may also use derivatives thereof that are readily decomposed, that is, the so-called masked polyisocyanates, such as, for example, the corresponding phenyl or tolylcarbamic acid esters or the malonic ester, caprolactam or oxime adducts of polyisocyanates and the like. Polyisocyanates which are used in the process according to the invention may also be partly replaced by monoisocyanates, generally in amounts of up to about 75 mol percent based on the polyisocyanate. Suitable monoisocyanates are, for example, methyl isocyanate, ethyl isocyanate, propyl isocyanate, butyl isocyanate, stearyl isocyanate and the like. Reaction products of low isocyanate content and exhibiting a low degree of branching are obtained in such a case. Polyisothiocyanates react in a manner similar to polyisocyanates and likewise may be used.

The process according to this invention is generally carried out by adding the two components, that is, the isocyanate and the Schiff's base, together at a low temperature, such as, for example, at room temperature of about 25°C. and then slowly heating the reactants to the temperature at which the desired extent of reaction is obtained. A temperature of about 200° to about 250°C. is usually the maximum temperature range at which the reaction can be carried out. Alternatively, however, in order to control the removal of heat in a more satisfactory manner, one of the two components may first be heated to the reaction temperature of the final stage and the second component may then be introduced at this temperature, or the two components may be introduced simultaneously at elevated temperature. The reaction may also be carried out in several stages since the number of equivalents of isocyanate entering into reaction per equivalent of azomethine depends not only on the reaction time but also on the reaction temperature. Up to about 10 mols of polyfunctional isocyanate may be used in the reaction per equivalent of azomethine. The process according to the invention may be carried out batch-wise or continuously. Low boiling starting materials are reacted in an autoclave under pressure, e.g. up to 20 atmospheres.

The reaction times can be shortened by addition of a catalytic amount of the usual catalysts for isocyanate reactions. Such catalysts include, for example, diethylaniline, zinc octoate, dibutyl tin dilaurate and the like.

The reaction times are generally from about 10 minutes to about 24 hours, depending on the temperature, the reactants and catalysts if used, although the reaction times may quite well possibly lie above or below these limits.

The process according to this invention may be carried out at any suitable reaction temperature such as, for example, at temperatures of from about −30°C. to about 250°C., preferably at a temperature of from −10°C. to 200°C.

The reaction may also be carried out in any suitable solvent. Suitable solvents include, for example, chloroform, diethylether, acetone, benzene, phenol, cresol, acetonitrile, ethyl acetate, trichlorobenzene, xylene, nitrobenzene, dimethylsulphoxide and the like. The reaction may, however, also be carried out in the absence of a solvent if desired.

The new compounds prepared by the process according to the invention contain at least one free isocyanato group available for further reactions, for example, for dimerization, trimerization, amidine formation or for reaction with compounds that contain reactive hydrogen atoms such as, for example, with ureas, amides, amines, alcohols, mercaptans and CH—acidic compounds.

Thus, for example, synthetic resins which no longer contain free isocyanato groups, are obtained by heating to elevated temperatures optionally with the addition of catalysts. Mixtures of these new compounds with polyfunctional alcohols, which can be applied as paints in suitable solvents, yield clear, transparent lacquer films. Foam plastics are obtained by reacting the products of the process with polyethers, polyesters and amines with the addition of suitable blowing agents according to methods known to those skilled in the art.

The polyisocyanates prepared according to the invention also can serve as bonding agents when used in mixtures with polyols or polymers such as rubber or chloroprene by methods known in the art.

The invention is further illustrated but is not intended to be limited by the following examples in which all parts and percentages are by weight unless otherwise specified.

EXAMPLE 1

About 9.8 parts of N-phenyl-acetophenone-azomethine and 34.8 parts of tolylene-2,4-diisocyanate are heated to about 100°C. for about one hour. A yellow viscous liquid having an isocyanate content of 29.2 percent is obtained, corresponding to isocyanate uptake of 1.8 equivalents per mol of azomethine.

EXAMPLE 2

About 9.8 parts of N-phenyl-acetophenone-azomethine and about 34.8 parts of tolylene-2,4-diisocyanate are heated to about 150°C. for about one hour. A brown resin is obtained which has an isocyanate content of 15.6 percent, corresponding to a reaction of 4.7 equivalents of isocyanate per mol of azomethine.

EXAMPLE 3

About 48 parts of phenylisocyanate are introduced dropwise at about 100°C. into about 35 parts of N-phenyl-cyclohexanone-azomethine. The reaction mixture is then stirred for about 2 hours at this temperature. The temperature is raised to about 110°C., and about 70 parts of tolylene diisocyanate (isomeric mixture of 2,4- and 2,6-isomers in the ratio of 65: 35 percent by weight) are added dropwise. The reaction mixture is then stirred for about 4 hours at this temperature. A pale yellow resin having an isocyanate content of 10.1 percent is obtained.

EXAMPLE 4

About 268 parts of N-cyclohexyl-cyclohexanone-azomethine are added dropwise to about 1010 parts of 1,6-hexamethylene diisocyanate under an atmosphere of nitrogen at about 20° to about 25°C. The reaction mixture is heated to about 155°C. over the course of about 2 hours. After about half an hour at this temperature, a clear pale liquid is obtained which becomes viscous when cold. The isocyanate content is 24.4 percent, corresponding to an uptake of 3.0 equivalents of isocyanate per mol of azomethine.

If the reaction mixture is heated for a total of about 2 hours to about 155°C., the liquid becomes highly viscous and the isocyanate content of the product is 19.3 percent, corresponding to a reaction of 4.1 equivalents of isocyanate per mol of azomethine. The IR spectrum shows the following characteristic bands: NH: 3230 cm$^{-1}$; —N=C=O: 2260 cm$^{-1}$; —CO—NH—; 1645 cm$^{-1}$ and 1525 cm$^{-1}$.

About 100 parts of this polyisocyanate together with about 75 parts of a hydroxyl-containing polyester of adipic acid, phthalic acid and trimethylolpropane are dissolved in ethyl glycol acetate. When this solution is applied to a surface and dried, it yields clear, hard lacquer films.

EXAMPLE 5

About 174 parts of tolylene-2,4-diisocyanate are preheated to about 155°C. About 43 parts of N-phenyl-cyclohexanone-azomethine are then added dropwise at this temperature and the mixture is then heated for about another hour. A yellow, brittle resin is obtained which has an isocyanate content of 16.2 percent.

EXAMPLE 6

About 281 parts of N-phenyl-cyclohexanone-azomethine are introduced dropwise over the course of about 1 hour into about 1625 parts of 4,4'-diisocyanate diphenylmethane at about 110°C. The reaction mixture is then stirred for about a further 14 hours at about 110°C. On cooling, a pale yellow, brittle resin of an isocyanate content of 13.9 percent is obtained. To render it suitable for use as a bonding agent, about 20 parts of this isocyanate are dissolved in about 80 parts of methylene chloride. The solutions of the bonding agent may be varied, that is, by the addition of about 10 parts of chloroprene or about 8 parts of a hydroxyl-containing polyester of diethylene glycol, trimethylolpropane and adipic acid.

EXAMPLE 7

About 43 parts of N-phenyl-cyclohexanone-azomethine are added dropwise at about 30°C. into about 174 parts of tolylene-2,4-diisocyanate. The reaction mixture is then heated to about 100°C. and is stirred at this temperature for about ½ hour. A yellow liquid is obtained, and this is introduced dropwise into a reaction flask preheated to about 155°C., where it is kept for about another hour at this temperature. The reaction product solidifies on cooling to form a yellow resin having an isocyanate content of 16.7 percent. The following groups can be identified in the IR spectrum: NH 3410 cm$^{-1}$; —N=C=O: 2260 cm$^{-1}$; —CO—NH—: 1650 cm$^{-1}$ and 1510 cm$^{-1}$. When a sample of this polyisocyanate is heated to about 210°C. for about 30 minutes, a pale brown polymer is obtained which no longer contains any free isocyanate groups.

EXAMPLE 8

About 33.6 parts of 1,6-hexamethylene diisocyanate and about 8.7 parts of N-phenylcyclohexanone-azomethine are heated together. The isocyanate content of the reaction product is as follows:

| | |
|---|---|
| after about 1 hour at about 100°C. | 32.9% |
| after about 1 hour at about 150°C. | 29.7% |
| after about 1 hour at about 200°C. | 13.0% |

EXAMPLE 9

About 33.6 parts of 1,6-hexamethylene diisocyanate and about 9.8 parts of N-phenyl-acetophenone-azomethine are heated together. The isocyanate content of the product is as follows:

| | |
|---|---|
| after about 1 hour at about 100°C. | 37.3% |
| after about 1 hour at about 150°C. | 32.4% |

EXAMPLE 10

About 43.6 parts of tolylene-2,4-diisocyanate and about 9 parts of N-cyclohexyl-cyclohexanone-azomethine are kept at about 150°C. for about one hour. A brown resin of isocyanate content 22.1 percent is obtained.

EXAMPLE 11

About 52.1 parts of tolylene-2,4-diisocyanate and about 8.7 parts of N-phenyl-cyclohexanone-azomethine are heated together. The isocyanate content of the reaction product is as follows:

| | |
|---|---|
| after about 0.5 hours at about 100°C. | 32.9% |
| after about 1 hour at about 150°C. | 24.7% |

EXAMPLE 12

About 1750 parts of 4,4'-diisocyanato diphenylmethane and about 173 parts of N-phenyl-cyclohexanone-azomethine are heated together at about 110°C. for about 11 hours. A viscous, dark yellow liquid is obtained which has an isocyanate content of 21.2 percent.

About 150 parts of the polyisocyanate prepared in this way yield a hard foam with good mechanical properties reacted with 100 parts of a hydroxyl-containing polyether, e.g. an addition product of propyleneoxide, trimethylol propane with an OH-number of 350, in the presence of 50 parts of chlorotrifluoromethane.

EXAMPLE 13

About 17 parts of N-phenyl-cyclohexanone-azomethine are introduced dropwise at about 120°C. into a solution of about 122 parts of tolylene-2,4-diisocyanate in about 140 parts of nitrobenzene. The reaction mixture is then stirred for about a further 7 hours at this temperature, and a clear, pale yellow liquid is obtained which has an isocyanate content of 14.3 percent.

It is to be understood that any of the components and conditions mentioned as suitable herein can be substituted for its counterpart in the foregoing examples and that although the invention has been described in considerable detail in the foregoing, such detail is solely for the purpose of illustration. Variations can be made in the invention by those skilled in the art without departing from the spirit and scope of the invention except as is set forth in the claims.

What is claimed is:

1. A process for the preparation of an isocyanato-containing reaction product which comprises reacting at a temperature of from about −30° to about 250°C. in the absence of moisture, a Schiff's base having the formula

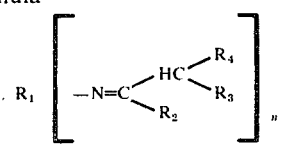

wherein $R_1$ is an n-functional radical and represents $C_1$ to $C_{36}$ alkyl, $C_5$ to $C_{10}$ cycloalkyl, up to $C_{14}$ aryl or aralkyl containing up to 3 aryl radicals substituted by $C_1$ to $C_5$ alkyl;

$R_2$ represents $C_1$ to $C_{36}$ alkyl, $C_5$ to $C_{10}$ cycloalkyl, up to $C_{14}$ aryl or aralkyl containing up to 3 aryl radicals substituted by $C_1$ to $C_5$ alkyl;

$R_3$ and $R_4$ represent hydrogen, $C_1$ to $C_{36}$ alkyl, $C_5$ to $C_{10}$ cycloalkyl, up to $C_{14}$ aryl or aralkyl containing up to 3 aryl radicals substituted by $C_1$ to $C_5$ alkyl;

The radicals $R_2$ and $R_3$ may join together to form a 5 to 7 membered cycloaliphatic ring; and $n$ represents an integer of from 1 to 3;

with from about 1 to about 10 mols per equivalent of Schiff's base of a compound selected from the group consisting of diisocyanates and triisocyanates.

2. The process of claim 1 wherein the Schiff's base is selected from the group consisting of N-phenyl-acetophenone-azomethine, N-phenyl-cyclohexanone-azomethine and N-cyclohexyl-cyclohexanone-azomethine and the polyisocyanate is selected from the group consisting of 2,4-tolylene diisocyanate, 2,6-tolylene diisocyanate, isomer mixtures of 2,4- and 2,6-tolylene diisocyanate, 1,6-hexamethylene diisocyanate and 4,4'-diisocyanato diphenylmethane.

3. A product produced by the process of claim 1.

4. A product produced by the process of claim 2.

* * * * *